United States Patent [19]
Massey et al.

[11] Patent Number: 5,688,826
[45] Date of Patent: Nov. 18, 1997

[54] EXCITATORY AMINO ACID DERIVATIVES

[75] Inventors: Steven Marc Massey; James Allen Monn; Matthew John Valli, all of Indianapolis, Ind.

[73] Assignee: Eli Lilly and Company, Indianapolis, Ind.

[21] Appl. No.: 749,140

[22] Filed: Nov. 14, 1996

Related U.S. Application Data

[60] Provisional application No. 60/006,864, Nov. 10, 1995.

[51] Int. Cl.$^6$ .................. A61K 31/38; C07D 307/77
[52] U.S. Cl. .................. 514/443; 514/409; 514/412; 514/462; 514/469; 548/410; 548/452; 549/57; 549/344
[58] Field of Search .................. 514/409, 412, 514/443, 462, 469; 548/410, 452; 549/57, 344

[56] References Cited

U.S. PATENT DOCUMENTS

| | | | |
|---|---|---|---|
| 2,572,842 | 10/1951 | MacDonald | 514/409 |
| 4,536,330 | 8/1985 | Doden et al. | 514/409 |

FOREIGN PATENT DOCUMENTS

| | | |
|---|---|---|
| 696577 | 2/1996 | European Pat. Off. |
| WO 95/15940 | 6/1995 | WIPO |
| WO 96/04900 | 2/1996 | WIPO |
| WO 96/04901 | 2/1996 | WIPO |
| WO 96/05175 | 2/1996 | WIPO |
| WO 96/07405 | 3/1996 | WIPO |

OTHER PUBLICATIONS

D. Schoepp, et al., "Selective Inhibition of Forskolin–stimulated Cyclic AMP Formation in Rat Hoppocampus by a Novel mGluR Agonist, 2R, 4R–1–aminopyrrolidine–2,4–dicarboxylate", *Neuropharmacology*, 34(8), 843–850 (1995).

D. Schoepp, et al., "Pharmacological and functional characteristics of metabotropic excitatory amino acid receptors", *TiPS*, 11(12), 508–515 (1990).

D. Schoepp, et al., "Metabotropic glutamate receptors in brain function and pathology", *TiPS*, 14, 13–20 (1993).

Gillespie, et al., "The Reaction of Diazoalkanes with Thiophen", *Journal of the Chemical Society, Perkin Transactions I*, No. 7, 2624–2628 (1979).

*Primary Examiner*—Joseph McKane
*Assistant Examiner*—Richard S. Myers, Jr.
*Attorney, Agent, or Firm*—Martin A. Hay; David E. Boone

[57] ABSTRACT

Compounds for formula I

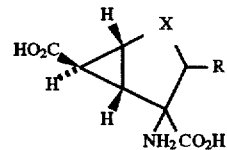

in which X represents O, NR$^a$, S, SO or SO$_2$ and R is as defined in the specification; and non-toxic metabolically labile esters or amides thereof; and pharmaceutically acceptable salts thereof are useful as modulators of metabotropic glutamate receptor function.

14 Claims, No Drawings

EXCITATORY AMINO ACID DERIVATIVES

This application claims the benefit of U.S. Provisional Application No. 60/006,864, filed Nov. 16, 1995.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, Ann. Rev. Pharmacol. Toxicol., 21, 165 (1981); Monaghan, Bridges, and Cotman, Ann. Rev. Pharmacol. Toxicol., 29, 365 (1989); Watkins, Krogsgaard-Larsen, and Honore, Trans. Pharm. Sci., 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, Trends in Pharmacol. Sci., 14, 13 (1993). Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

The present invention provides a compound of formula

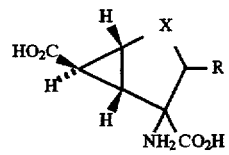

in which X represents O, $NR^a$, S, SO or $S_{O2}$; R represents a hydrogen atom; a (1–6C) alkyl group; a (2–6C) alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C) alkenyl or (2–6C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_nR^b$; n is 0 or 1; and $R^b$ is as defined for R; or a non-toxic metabolically labile ester or amide thereof; or a pharmaceutically acceptable salt thereof.

It will be appreciated that the compounds of formula I contain at least four asymmetric carbon atoms; three being in the cyclopropane ring and one or two being in the cyclopentane ring. The present invention includes all stereoisomeric forms of the compounds of formula I, including each of the individual enantiomers and mixtures thereof.

Preferably the compounds of formula I have the configuration shown below

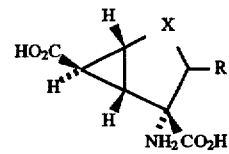

As used herein, the term (1–6C) alkyl means a straight chain or branched group. Examples of values for a (1–6C) alkyl group include (1–4C) alkyl such as methyl, ethyl, propyl, isopropyl, butyl and isobutyl.

The term (2–6C) alkenyl includes (2–4C) alkenyl, such as allyl.

The term (2–6C) alkynyl includes (2–4C) alkynyl, such as propynyl.

The term heteroaromatic group includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl.

The term aromatic group includes phenyl and a polycyclic aromatic carbocyclic ring such as naphthyl.

The term "optionally substituted", as used in the term "optionally substituted heteroaromatic or aromatic group", herein signifies that one or more substituents may be present, said substituents being selected from atoms and groups which, when present in the compound of formula I, do not prevent the compound of formula I from modulating metabotropic glutamate receptor function.

Examples of atoms and groups which may be present in an optionally substituted heteroaromatic or aromatic group are amino, hydroxy, nitro, halogeno, (1–6C) alkyl, (1–6C) alkoxy, (1–6C) alkylthio, carboxy, (1–6C) alkoxycarbonyl, carbamoyl, (1–6C) alkanoylamino, (1–6C) alkylsulphonyl, (1–6C) alkylsulphonylamino, optionally substituted phenyl, phenoxy, phenylthio, phenylsulphonyl, phenylsulphonylamino, toluenesulphonylamino, (1–6C) fluoroalkyl and (1–6C) fluoroalkoxy. Examples of particular values are amino, hydroxy, fluoro, chloro, bromo, iodo, methyl, methoxy, methylthio, carboxy, acetylamino, methanesulphonyl, nitro, acetyl, phenoxy, phenylthio, phenylsulphonyl, methanesulphonylamino and trifluoromethyl.

Examples of values for an optionally substituted aromatic group are 1-naphthyl, 2-naphthyl, phenyl, 2-biphenyl, 3-biphenyl, 4-biphenyl, 2-hydroxyphenyl, 3-hydroxyphenyl, 4-hydroxyphenyl, 2-fluorophenyl, 3-fluorophenyl, 4-fluorophenyl, 2,4-difluorophenyl, 3,4-difluorophenyl, pentafluorophenyl, 2-chlorophenyl, 3-chlorophenyl, 4-chlorophenyl, 2,4-dichlorophenyl, 3,4-dichlorophenyl, 3-chloro-4-fluorophenyl, 3,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2,3-dimethoxyphenyl, 2,5-dimethoxyphenyl, 3,4-dimethoxyphenyl, 3,5-dimethoxyphenyl, 2-trifluoromethylphenyl, 3-trifluoromethylphenyl, 4-trifluoromethylphenyl, 2-fluoro-3-trifluoromethylphenyl, 3-trifluoromethyl-4-fluorophenyl, 3-trifluoromethyl-5-fluorophenyl, 2-fluoro-5-trifluoromethylphenyl, 2-phenoxyphenyl, 3-phenoxyphenyl, 3-carboxyphenyl, and 4-carboxyphenyl.

The term "non-aromatic carbocyclic group" includes a monocyclic group, for example a (3–10C) cycloalkyl group, such as cyclopropyl, cyclobutyl, cyclopentyl, cyclohexyl, cycloheptyl, cyclooctyl, cyclononyl or cyclodecyl, and a fused polycyclic group such as 1-adamantyl or 2-adamantyl, 1-decalyl, 2-decalyl, 4a-decalyl, bicyclo[3,3,0]oct-1-yl, -2-yl or -3-yl, bicyclo[4,3,0]non-1-yl, -2-yl, -3-yl or -7-yl, bicyclo[5,3,0]dec-1-yl, -2-yl, -3-yl, -4-yl, -8-yl or -9-yl and bicyclo[3.3.1]non-1-yl, -2-yl, -3-yl or 9-yl.

The term "non-aromatic heterocyclic group" includes a 4 to 7 membered ring containing one or two heteroatoms selected from oxygen, sulphur and nitrogen, for example azetidin-1-yl or -2-yl, pyrrolidin-1-yl, -2-yl or -3-yl, piperidin-1-yl, -2-yl, -3-yl or -4-yl, hexahydroazepin-1-yl, -2-yl, -3-yl or -4-yl, oxetan-2-yl or -3-yl, tetrahydrofuran-2-yl or -3-yl, tetrahydropyran-2-yl, -3-yl or -4-yl, hexahydrooxepin-2-yl, -3-yl or -4-yl, thietan-2-yl or -3-yl, tetrahydrothiophen-2-yl, or -3-yl, tetrahydrothiopyran-2-yl, -3-yl or -4-yl, hexahydrothiepin-2-yl, -3-yl or -4-yl, piperazin-1-yl or -2-yl, morpholin-1-yl, -2-yl or -3-yl, thiomorpholin-1-yl, -2-yl or -3-yl, tetrahydropyrimidin-1-yl, -2-yl, -4-yl or -5-yl, imidazolin-1-yl, -2-yl or -4-yl, imidazolidin-1-yl, -2-yl or -4-yl, oxazolin-2-yl, -3-yl, -4-yl or -5-yl, oxazolidin-2-yl, -3-yl, -4-yl or -5-yl, thiazolin-2-yl, -3-yl, -4-yl or -5-yl, or thiazolidin-2-yl, -3-yl, -4-yl or -5-yl.

The term "a non-aromatic monocyclic carbocyclic group fused with one or two monocyclic aromatic or heteroaromatic groups" includes a (3–10C) cycloalkyl group fused with a benzene ring or a an aromatic 5–6 membered ring containing from one to four heteroatoms selected from oxygen, sulfur and nitrogen, such as indanyl, 1,2,3,4-tetrahydronaphth-1-yl or -2-yl, 5,6,7,8-tetrahydroquinolin-5-yl, -6-yl, -7-yl or 8-yl, 5,6,7,8-tetrahydroisoquinolin-5-yl, -6-yl, -7-yl or 8-yl, 4,5,6,7-tetrahydrobenzothiophen-4-yl, -5-yl, -6-yl or -7-yl, dibenzo[2,3,6,7]cycloheptan-1-yl or -4-yl, dibenzo[2,3,6,7]cyclohept-4-en-1-yl or -4-yl, or 9-fluorenyl.

The term "a non-aromatic monocyclic heterocyclic group fused with one or two monocyclic aromatic or heteroaromatic groups" includes a 4 to 7 membered ring containing one or two heteroatoms selected from oxygen, sulphur and nitrogen, fused with a benzene ring or a an aromatic 5–6 membered ring containing from one to four heteroatoms selected from oxygen, sulfur and nitrogen, such as 2,3-dihydrobenzopyran-2-yl, -3-yl or -4-yl, xanthen-9-yl, 1,2,3, 4-tetrahydroquinolin-1-yl, -2-yl, -3-yl or -4-yl, 9,10-dihydroacridin-9-yl or -10-yl, 2,3-dihydrobenzothiopyran-2-yl, -3-yl or -4-yl, or dibenzothiopyran-4-yl.

An example of a value for R when it represents an optionally substituted heteroaromatic group is 2-pyrimidyl.

When R represents an optionally substituted aromatic group, it preferably represents a 2-naphthyl group or a phenyl group which is unsubstituted or substituted by one or two substituents selected independently from halogen, (1–4C) alkyl and (1–4C) alkoxy.

Examples of values for R when it represents an optionally substituted aromatic group are 2-naphthyl, phenyl, 2-fluorophenyl, 3-fluorophenyl, 4-fluorophenyl, 3,4-difluorophenyl, pentafluorophenyl, 2-chlorophenyl, 3-chlorophenyl, 4-chlorophenyl, 3,4-dichlorophenyl, 2,5-dichlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 3-trifluoromethylphenyl and 4-trifluoromethylphenyl.

Examples of values for R when it represents a substituted (1–6C) alkyl, (2–6C) alkenyl or (2–6C) alkynyl group are phenyl (1–4C) alkyl groups and diphenyl (1–4C) alkyl which are unsubstituted or substituted on phenyl by one or two substituents selected independently from halogen, (1–4C) alkyl, (1–4C) alkoxy and phenyl. More particularly, R may represent a benzyl group in which the phenyl ring is unsubstituted or substituted by one or two substituents selected independently from fluoro, chloro, methyl, isopropyl, methoxy and phenyl; such as 3-chloro-4-fluorobenzyl, 4-fluorobenzyl, 3-methylbenzyl, 4-fluoro-3-methylbenzyl, 2,3-difluorobenzyl, 3,4-difluorobenzyl and 3-chlorobenzyl.

A preferred value for R is hydrogen.

A preferred value for $R^a$ is hydrogen.

Preferably X represents O or S.

Particularly preferred compounds are 1SR,4SR,5RS,6SR-4-amino-2-oxabicyclo[3.1.0]hexane-4,6-dicarboxylic acid and 1SR,4SR,5RS,6SR-4-amino-2-thiabicyclo[3.1.0]hexane-4,6-dicarboxylic acid. (−)-1R,4R,5S,6R-4-amino-2-oxabicyclo[3.1.0]hexane-4,6-dicarboxylic acid is especially preferred. These compounds have been found to be potent agonists of glutamate at cAMP-linked metabotropic glutamate receptors. Another preferred compound is 1SR, 3RS,4SR,5RS, 6SR-3-(3-chloro-4-fluoro)benzyl-4-amino-2-oxabicyclo[3.1.0]-hexane-4,6-dicarboxylic acid.

The present invention includes pharmaceutically acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylammonium, sodium, methylammonium, calcium, and the like salts.

Non-toxic metabolically labile ester and amide of compounds of formula I are ester or amide derivatives of compounds of formula I that are hydrolyzed in vivo to afford said compound of formula I and a pharmaceutically acceptable alcohol or amine. Examples of metabolically labile esters include esters formed with (1–6C) alkanols in which the alkanol moiety may be optionally substituted by a (1–8C) alkoxy group, for example methanol, ethanol, propanol and methoxyethanol. Examples of metabolically labile amides include amides formed with amines such as methylamine.

According to another aspect, the present invention provides a process for the preparation of a compound of formula I which comprises (a) hydrolyzing a compound of formula

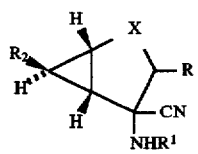

II in which R¹ represents a hydrogen atom or an acyl group and R² represents a carboxyl group or an esterified carboxyl group, or a salt thereof;

(b) hydrolyzing a compound of formula

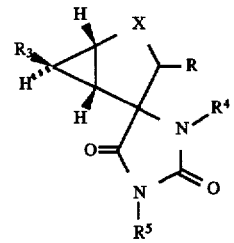

III in which R³ represents a carboxyl group or an esterified carboxyl group, and R⁴ and R⁵ each independently represent a hydrogen atom, a (2–6C) alkanoyl group, a (1–4C) alkyl group, a (3–4C) alkenyl group or a phenyl (1–4C) alkyl group in which the phenyl is unsubstituted or substituted by halogen, (1–4C) alkyl or (1–4C) alkoxy, or a salt thereof; or (c) deprotecting a compound of formula

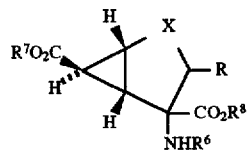

IV in which $R^6$ represents a hydrogen atom or a nitrogen protecting group and each of $R^7$ and $R^8$ independently represent a hydrogen atom or a carboxyl protecting group, or a salt thereof;

whereafter, if necessary and/or desired
(i) resolving the compound of formula I;
(ii) converting the compound of formula I into a non-toxic metabolically labile ester or amide thereof; and/or;
(iii) converting the compound of formula I or a non-toxic metabolically labile ester or amide thereof into a pharmaceutically acceptable salt thereof.

The protection of carboxylic acid and amine groups is generally described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include alkyl groups such as methyl, ethyl, t-butyl and t-amyl; aralkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl. Examples of amine protecting groups include acyl groups, such as groups of formula $R^{11}CO$ in which $R^{11}$ represents (1–6C) alkyl, (3–10C) cycloalkyl, phenyl(1–6C) alkyl, phenyl, (1–6C) alkoxy, phenyl(1–6C) alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonylamino, and (1–6C) fluoroalkyl.

The compounds of formula II are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water and at a temperature in the range of from 50° to 200° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50° to 150° C.

Preferred values for $R^1$ are hydrogen and (2–6C) alkanoyl groups, such as acetyl.

Preferred values for $R^2$ when it represents an esterified carboxyl group are (1–6C) alkoxycarbonyl groups such as ethoxycarbonyl.

The compounds of formula IV may be deprotected by a conventional method. Thus, an alkyl carboxyl protecting group may be removed by hydrolysis. The hydrolysis may conveniently be performed by heating the compound of formula V in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from 10° to 300 ° C. An aralkyl carboxyl protecting group may conveniently be removed by hydrogenation. The hydrogenation may conveniently be effected by reacting the compound of formula V with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° to 100° C. An acyl, amine protecting group is also conveniently removed by hydrolysis, for example as described for the removal of an alkyl carboxyl protecting group.

The compounds of formula II may be prepared by reacting a compound of formula V

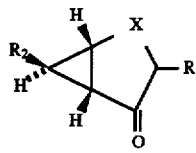

with an alkali metal cyanide, such as lithium, sodium or potassium cyanide, and an ammonium halide, such as ammonium chloride, conveniently in the presence of ultrasound. Thus, the ammonium halide is mixed with chromatography grade alumina in the presence of a suitable diluent such as acetonitrile. The mixture is then irradiated with ultrasound, whereafter the compound of formula V is added, and the mixture is again irradiated. The alkali metal cyanide is then added, followed by further irradiation with ultrasound.

The resultant mixture of diastereoisomeric aminonitriles is then reacted with an acylating agent, such as acetyl chloride in the presence of a suitable base, for example an amine such as ethyl diisopropylamine and in the presence of a suitable solvent, such as dichloromethane, to afford a mixture of diastereomeric acylamino nitriles. The desired diastereoisomer is conveniently separated from this mixture, for example by chromatography.

The compounds of formula III may be prepared by reacting a compound of formula V with an alkali metal cyanide, such as lithium, sodium or potassium cyanide, and ammonium carbonate or ammonium carbamate. Convenient solvents include alcohols, such as methanol, aqueous methanol and aqueous ethanol. Conveniently the reaction is performed at a temperature in the range of from 10° to 150° C. If desired, the compounds of formula III may then be alkylated, for example using an appropriate compound of formula $R^4Cl$ and/or $R^5Cl$.

The compounds of formula III may conveniently be resolved prior to hydrolysis. Thus, for example, a compound of formula III in which $R^2$ represents a carboxyl group may be resolved by treatment with an optically active amine, such as (R)-2-phenylglycinol.

The compounds of formula V in which X represents O may be prepared by cyclising a compound of formula

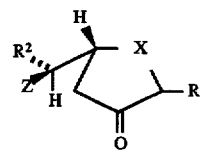

in which Z represents a leaving atom or group, for example an iodine atom. The reaction is conveniently performed in the presence of a base, such as 1,8-diazabicyclo[5.4.0]undec-7-ene. Suitable solvents include ethers, such as tetrahydrofuran. The temperature is conveniently in the range of from 0° to 100° C.

The compounds of formula VI may be prepared by oxidising a compound of formula

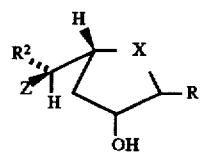

The oxidation is conveniently effected using an appropriate conventional oxidation method, for example, using oxalyl chloride in dimethyl sulfoxide or (when X is O, $NR^a$ or $SO_2$ only) chromium trioxide in sulfuric acid (Jones reagent).

The compounds of formula VIa may be prepared by the method described in J. Amer. Chem. Soc., 110 (14), 1988, pages 4533–4540.

The compound of formula V may also be prepared by oxidizing a compound of formula

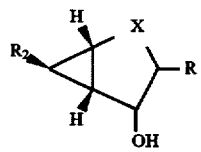

The oxidation may conveniently be effected by reacting the compounds of formula VII with dimethyl sulfoxide in the presence of an activating agent, such as oxalyl chloride, followed by treatment with a base, such as triethylamine. The reaction is conveniently performed at a temperature in the range of from –80° to –20° C.

The compounds of formula VII may be prepared by reacting a compound of formula

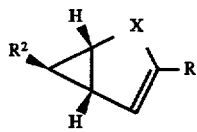

with a hydroborating agent, such as borane or thexylborane, followed by an oxidizing agent, such as hydrogen peroxide in the presence of a base, such as sodium hydroxide or an aqueous buffer in the pH range of from 5 to 14. The temperature is conveniently in the range of from –20° to 25° C. The reaction may generally be performed according to the methods described in J. Am. Chem. Soc. 1986, 108, 2049 and J. Am. Chem. Soc., 1991, 113, 4037.

The compounds of formula IX may be prepared by reacting a compound of formula

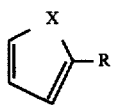

with a compound of formula $R^2CN_2$ in the presence of a transition metal catalyst, such as a rhodium or copper catalyst. The reaction may generally be performed according to the methods described in J. Chem. Soc. Perkin Tran I, 1979, 2624; Tetrahedron, 1971, 27, 2957. Justus Liebigs Ann. Chem. 1963, 668, 19; and Tet. Let. 1964, 2185.

Compounds of formula V in which R represents a (1–6C) alkyl or a substituted (1–6C) alkyl group may also be prepared from the corresponding compounds of formula V in which R represents a hydrogen atom by reaction with the appropriate aldehyde, for example in the presence of pyrrolidine, followed by hydrogenation of the resultant alkylidene adduct, for example using Raney nickel or palladium on carbon as catalyst.

Many of the intermediates described herein, for example the compounds of formula II, III and IV are believed to be novel, and are provided as further aspects of the invention.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of formula I or a pharmaceutically acceptable metabolically labile ester or amide thereof, or a pharmaceutically acceptable salt thereof.

The formula I compounds of the present invention are also believed to have the ability to treat a variety of other neurological disorders in mammals that are associated with glutamate dysfunction, including muscular spasms, convulsions, migraine headaches, urinary incontinence, nicotine withdrawal, psychosis, (such as schizophrenia), drug tolerance, withdrawal and cessation (i.e. opiates, benzodiazepines, nicotine, cocaine or ethanol), smoking cessation, anxiety and related disorders (e.g. panic attack and stress-related disorders), emesis, brain edema, chronic pain, sleep disorder, Toeurettes syndrome, attention deficit disorder, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester or amide thereof, or a pharmaceutically acceptable salt thereof.

Experiments were performed to demonstrate the ability of the formula I compounds to affect the excitatory amino acid receptors. The affinity for metabotropic glutamate receptors was demonstrated by the selective displacement of 1S,3R-ACPD-sensitive [$^3$H]glutamate binding to rat brain cell membranes. The binding of [$^3$H]glutamate was conducted with crude membranes of rat forebrain as described by Schoepp and True. Schoepp and True, Neuroscience Lett., 145, 100–104 (1992) and Wright et al., J. Neurochemistry 63:938–945 (1994). For example, the compound of Example 1 was found to have an $IC_{50}$ of 0.055 µM in this test.

Based on studies of receptor mediated changes in intracellar second messengers, metabotropic glutamate receptor are either coupled to enhanced phosphoinositide hydrolysis or decreases in forskolin-stimulated cAMP formation. Compounds may also be tested for ability to prevent inhibition of forskolin (30 µM)-stimulated cAMP formation by an mGluR agonist (1S,3R-ACPD, 20 µM) using slices of the rat hippocampus as described by D. D. Schoepp and B. G. Johnson, Neurochemistry International 22: 277–283 (1993) and human mGluR2 expressing non-neuronal cells (D. D. Schoepp et al., Neuropharmacology, 34, 843–850, 1995).

According to another aspect, the present invention provides a method of modulating one or more metabotropic glutamate receptor functions in a warm-blooded mammal which comprises administering an effective amount of a compound of formula I, or a non-toxic metabolically labile ester or amide thereof, or a pharmaceutically acceptable salt thereof.

The compounds of the present invention are preferably formulated prior to administration. Therefore, another aspect of the present invention is a pharmaceutical formulation comprising a compound of formula I and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1
Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
| --- | --- |
| Active Ingredient | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| Active Ingredient | 100 mg |
| Mannitol | 100 mg |
| 5 N Sodium hydroxide | 200 ml |
| Purified water to total | 5 ml |

The following Examples illustrate the invention.

The following abbreviations are used in the Examples: EtOAc, ethyl acetate; THF, tetrahydrofuran; EtOH, ethanol; TLC, thin layer chromatography; GC, gas chromatography; HPLC, high pressure liquid chromatography; m-CPBA, m-chloroperbenzoic acid; $Et_2O$, diethyl ether; DMSO, dimethyl sulfoxide; DBU, 1,8-diazabicyclo[5.4.0]undec-7-ene, MTBE, methyl t-butyl ether; and FDMS, field desorption mass spectrometry.

EXAMPLE 1

1SR,4SR,5RS,6SR-4-Amino-2-Oxabicyclo[3.1.0]hexane-4,6-dicarboxylic Acid (a) 2SR-1,2-O-Isopropylidene-butane-1,2,4-triol. A solution of 1,2,4-butanetriol (53 g, 500 mmol) in acetone (1 L) was treated in one portion with p-toluenesulfonic acid monohydrate (4.75 g, 25 mmol) and stirred at ambient temperature overnight. Triethylamine (2.5 g, 25 mmol) was added in one portion and the resulting reaction mixture concentrated in vacuo to yield the crude product. Purification via HPLC (10% EtOAc/hexanes to 50% EtOAC/hexanes) afforded the title compound (53.1 g, 363 mmol) 73%. FDMS: $M^+ +1=147$. Anal. calcd. for $C_7H_{14}O_3 \cdot 0.5 H_2O$: C, 54.18; H, 9.74. Found: C, 54.50; H, 9.56.

(b) 5SR,E-Ethyl 5,6-O-Isopropylidene-5,6-dihydroxy-2-hexenoate. (DMSO (56.65 g, 725 mmol) was added dropwise to a −78° C. solution of oxalyl chloride (48.32 g, 380.7 mmol) in $CH_2Cl_2$ (1 L) and stirred for 15 minutes. Subsequently, a solution of the product of step (a) (53 g, 362.6 mmol) in $CH_2Cl_2$ (400 mL) was added dropwise at a rate to maintain reaction temperature ≦−60° C. N,N-Diisopropylethylamine (140.6 g, 1087 mmol) was added dropwise and the resulting slurry allowed to warm to ambient temperature as it stirred for 2 hours to afford crude O-Isopropylidene-4-oxo-(SR)butane-1,2-diol. The reaction mixture was chilled to 0° C., (carbethoxymethylene)-triphenylphosphorane (252.5 g, 725 mmol) was added in one portion, and allowed to warm to ambient temperature as it stirred overnight. The reaction mixture was diluted with diethylether, washed consecutively with $H_2O$, aqueous $NaHSO_4$, and brine, dried over $MgSO_4$ and concentrated in vacuo to yield the crude product. The product was triturated in $Et_2O$, the $Ph_3P=O$ removed via filtration, and the filtrate concentrated in vacuo to yield the crude product. Purification via HPLC (10% EtOAc/hexanes to 50% EtOAC/hexanes) afforded the Z isomer (1.52 g, 7.1 mmol) 2% and the title E isomer (56.55 g, 264 mmol) 73%. Z Isomer: FDMS: $M^+ +1=215$. Anal. calcd. for $C_{11}H_{18}O_4 \cdot 0.25 H_2O$: C, 60.39; H, 8.52. Found: C, 60.49; H, 8.28. E isomer: FDMS: $M^+ +1=215$. Anal. calcd. for $C_{11}H_{18}O_4$: C, 61.66; H, 8.47. Found: C, 61.44; H, 8.24.

(c) 5SR,E-Ethyl (SR,E) 5,6-Dihydroxy-2-hexenoate. A solution of the product of step (b) (46.4 g, 216.6 mmol) in THF (700 mL) was treated in one portion with 1N HCl (500 mL) and stirred at ambient temperature overnight. EtOAc and NaCl were added and the resulting slurry stirred vigorously for two hours. The reaction mixture was partitioned in a separatory funnel and the product extracted with EtOAc. All organics were combined, washed with brine, dried over $MgSO_4$, and concentrated in vacuo to yield the crude diol. Purification via HPLC (25% EtOAc/hexanes to 95% EtOAc/hexanes) afforded the title compound (30.52 g, 175 mmol) 81%. FDMS: $M^+ +1=175$. Anal. calcd. for $C_8H_{14}O_4 \cdot 0.25 H_2O$: C, 53.77; H, 8.18. Found: C, 53.88; H, 7.95.

(d) 2SR,4RS-Ethyl 2-[(4-Hydroxytetrahydrofuran-2-yl)]-2-iodoacetate. A solution of the product of step (c) (30.41 g, 74.6 mmol) in diethyl ether (1.5 L) at ambient temperature was treated consecutively with $NaHCO_3$ (44.0 g, 524 mmol) then $I_2$ (100.8 g, 788 mmol), and the resulting reaction mixture stirred until complete by TLC. Aqueous $Na_2S_2O_3$ was added to the reaction mixture and product extracted with $Et_2O$. All organics were combined, washed with $Na_2S_2O_3$, $H_2O$, then brine, dried over $Na_2SO_4$ and concentrated in vacuo to yield the crude product. Purification via HPLC (5% EtOAc/hexanes to 50% EtOAc/hexanes) afforded the title compound (29.05 g, 97 mmol) 55%. FDMS: $M^+ +1=301$. Anal. calcd. for $C_8H_{13}IO_4 \cdot 1.0 H_2O$: C, 30.21; H, 4.75. Found: C, 30.23; H, 4.43.

(e) 2SR-Ethyl 2-[(4-oxo-tetrahydrofuran-2-yl)]-iodoacetate. A solution of the product of step (d) (28.5 g, 95 mmol) in $CH_2Cl_2$ (500 mL) with 3 Å sieves was treated in one portion with pyridinium chlorochromate (91.5 g, 425 mmol) and stirred at ambient temperature overnight. The reaction mixture was diluted with $Et_2O$ and filtered through celite®. The filtrate was partitioned with 1N HCl and the product extracted with $Et_2O$. All organics were combined, washed with 1N HCl, and brine, dried over $MgSO_4$, and concentrated in vacuo to yield the crude product. Purification via HPLC (10% EtOAc/hexanes to 50% EtOAc/hexanes) afforded the title compound (17.9 g, 60.1 mmol) 63%. FDMS: $M^+=298$. Anal. calcd. for $C_8H_{11}IO_4 \cdot 0.5 H_2O$: C, 31.29; H, 3.94. Found: C, 31.16; H, 3.75.

(f) 1SR,5SR,6SR-Ethyl 2-oxabicyclo[3.1.0]hexan-4-one-6-carboxylate. A solution of the product of step (e) (5.25 g, 17.6 mmol) in THF (50 mL) was treated by dropwise addition of a solution DBU (2.82 g, 18.5 mmol) in THF (10 mL) and the resulting reaction mixture stirred at ambient temperature for 1 hour. The reaction mixture was reduced in vacuo, partitioned between $Et_2O$ and 1N HCl, and the product extracted with $Et_2O$. All organics were combined, washed with brine, dried over $MgSO_4$, and concentrated in vacuo to yield the crude product. Purification via HPLC (10% EtOAc/hexanes to 50% EtOAc/hexanes) afforded the title compound (1.47 g, 8.63 mmol) 49%. FDMS: $M^+=170$ Anal. calcd. for $C_8H_{10}O_4 \cdot 0.1 H_2O$: C, 55.88; H, 5.98. Found: C, 55.73; H, 5.81.

(g) 1SR,4SR,5RS,6SR-Diethyl 4-(aminobenzyloxycarbonyl)-2-oxabicyclo[3.1.0]-hexane-4,6-dicarboxylate. A solution of the product of step (f) (3.0 g, 17.6 mmol) in a 1:1 mixture of EtOH:$H_2O$ (50 mL total volume) was treated consecutively with $NH_2CO_2NH_4$ (4.13 g, 52.9 mmol), then KCN (1.72 g, 26.4 mmol) and warmed at 55° C. for 40 hours. NaOH (4.0 g, 100 mmol) added in one portion to the reaction and warmed under reflux for 48 hours. The reaction mixture was concentrated in vacuo and the crude aminodiacid reconstituted in $H_2O$. The aqueous component was washed with $Et_2O$ (3×), chilled to 0° C., and acidified to pH=1 with conc. HCl. The aqueous component was washed with $Et_2O$ (3X), basified to pH=10 with $NaHCO_3$, and concentrated to dryness in vacuo. The solids were reconstituted in a 1:1 mixture of THF:$H_2O$ (100 mL total volume), stirred at 0° C. as benzylchloroformate (4.50 g, 26.4 mmol) was added dropwise, and allowed to warm to ambient temperature as it stirred for 48 hours. The reaction mixture was diluted and washed with Et₂O. The aqueous layer was acidified to pH=1 with conc. HCl, and partitioned with NaCl and EtOAc. The product was extracted with EtOAc, dried over MgSO4, and concentrated in vacuo to yield the crude N-CBZ diacid. This intermediate was reconstituted in CH3CN and treated consecutively with triethylamine (5.6 g 56 mmol) then iodoethane (6.5 g, 42 mmol) and warmed at 50° C. for 48 hours. The reaction mixture was diluted with Et₂O and partitioned with 1N HCl. The product was extracted with Et20, washed with brine, dried over MgSO4 and concentrated in vacuo to yield the crude product which was purified by HPLC (10% EtOAc/hexanes to 50% EtOAc/hexanes) to afford the title compound (1.18 g, 3.13 mmol) 18%. FDMS: M⁺=377 Anal. calcd. for C19H23NO7: C, 60.47; H, 6.14; N, 3.71. Found: C, 60.61; H, 6.44; N, 3.75. (h) A solution of the product of step (g) (0.71 g, 1.86 mmol) in 2N NaOH (20 mL) was warmed under reflux for 3 days. The reaction mixture was partitioned and washed with EtOAc. The resulting aqueous component was subsequently acidified with 6N HCl and washed with EtOAc. All organics were discarded. The aqueous phase was concentrated to dryness, reconstituted in H₂O and the pH adjusted to 14 with 1N NaOH. The resulting solids were removed by filtration and the filtrate reduced in vacuo. The pH was adjusted to 2 with 1N HCl, applied to Dowex®50X8–100 cation exchange resin and eluted with 10% pyridine/H₂O to afford the title compound (0.25 g, 1.34 mmol) 72%. mp=dec>200° C. FDMS: M⁺+1= 188. Anal. calcd. for C₇H₉NO₅: C, 44.92; H, 4.85; N, 7.48. Found: C, 44.69; H, 4.73; N, 7.25.

EXAMPLE 2

1S,4S,5R,6S Enantiomer and 1R,4R,5S,6R enantiomer of 4-amino-2-oxabicyclo[3.1.0]hexane-4,6-dicarboxylic Acid (a) 2SR-Ethyl 2-[(4-oxo-tetrahydrofuran-2-yl)]-iodoacetate. A 0° C. solution of the product of Example 1, step (d) (34.0 g, 113 mmol) in acetone (500 mL) was treated by dropwise addition of the Jones reagent (225 mL, 450 mmol) at a rate to maintain the reaction temperature ≦15° C. Upon complete addition the reaction was allowed to warm to ambient temperature as it stirred for 3 hours. 2-Propanol (30 mL) was added dropwise to quench the reaction. The reaction volume was reduced in vacuo and the product extracted with Et₂O. All organics were combined, washed with brine, dried (MgSO₄), and purified by preparation HPLC (10% EtOAc/hexanes to 50% EtOAc/hexanes) to afford 24.6 g, (82.5 mmol, 73%) of the title compound. FDMS: M⁺=298. Anal. calcd. for C₈H₁₁IO4: C, 32.24; H, 3.72. Found: C, 32.37; H, 3.82.

(b) 1SR,5SR,6SR-Ethyl-2-oxabicyclo[3.1.0]hexan-4-one-6-carboxylate. A 10° C. solution of the product of step (a) (39.6 g, 133 mmol) in EtOAc (1.5 L) was treated by dropwise addition of a solution DBU (25.28 g, 166 mmol) in EtOAc (100 mL) and the resulting reaction mixture stirred at 10°–15° C. until the reaction was judged complete by TLC and GC. The reaction mixture was acidified with 1N HCl, and the product extracted with EtOAc. All organics were combined, washed with Na₂S₂O₃ then brine, dried over MgSO₄, and concentrated in vacuo to yield a crude product. Purification via HPLC (5% EtOAc/hexanes to 50% EtOAc/hexanes) afforded the title compound (14.7 g, 86.3 mmol) 52%. FDMS: M⁺=170 Anal. calcd. for C₈H₁₀O₄.0.25 H₂O: C, 55.01; H, 6.06. Found: C, 55.32; H, 5.76.

(c) 1SR,4SR,5RS,6SR-Ethyl-(4-spiro-5'-hydantoin)-2-oxabicyclo-[3.1.0]-hexane-6-carboxylate. A solution of the product from step (b) (14.0 g, 82 mmol) in 100% EtOH (100 mL) and H₂O (40 mL) at ambient temperature, was treated consecutively with (NH₄)₂CO₃ (16.0 g, 205 mmol), and KCN (6.70 g, 103 mmol) and warmed at 35° C. for 1 hour. The reaction mixture was cooled to 0° C., and the product precipitated from solution at pH=4 by dropwise addition of 5N HCl. The solids were collected via vacuum filtration, washed with 2-propanol and dried at 80° C. under vacuum to afford 12.24 g, (51 mmol, 62%) of the title compound. mp=161°–163° C. FDMS: M⁺=240. Anal. calcd. for C₁₀H₁₂N₂O₅-0.60 H2O: C, 47.85; H, 5.30; N, 11.16. Found: C, 47.53; H, 4.89; N, 10.91.

(d) 1SR,4SR,5RS,6SR-4-(spiro-5'-hydantoin)-2-oxabicyclo-[3.1.0]hexane-6-carboxylic acid. A solution of the product from step (c) (8.5 g, 35.4 mmol) in 2N NaOH (70 mL) was stirred at ambient temperature for 3 hours. The reaction mixture was cooled to 0° C., and 5.0 g (23.6 mmol, 67%) of the product precipitated from solution at pH=1 by dropwise addition of conc. HCl. The aqueous filtrate was saturated with NaCl and extracted with EtOAc to yield an additional 2.3 g (10.8 mmol, 16%) of the desired product. Total combined yield of the title compound was 7.3 g (34.4 mmol, 97%). mp=258°–261° C. FDMS: M⁺+1=213. Anal. calcd. for C₈H₈N₂O₅: C, 45.29; H, 3.80; N, 13.20. Found: C, 45.00; H, 3.65; N, 12.99.

(e) 1R,4R,5S,6R-(–)-4-(spiro-5'-hydantoin)-2-oxabicyclo-[3.1.0]hexane-6-carboxylate. A 65° C. solution of the racemic mixture of compounds prepared as described in Step (d) (6.67 g, 31.4 mmol) in EtOH (2 L) was treated with a solution of R-(–)-2-phenylglycinol (4.74 g, 34.5 mmol) in EtOH (500 mL), and the resulting reaction mixture heated under reflux until dissolution occurred. The reaction mixture was allowed to cool to ambient temperature as it stirred overnight. 4.20 g (12 mmol) of the product was collected in ≧95% ee via vacuum filtration. One additional recrystallization from EtOH afforded 3.83 g (11 mmol, 35%) of the chiral salt in >99.5% ee. α_D=–111° (c=0.1, H2O). mp=198°–201° C. Anal. calcd. for C₁₆H₁₉N₃O₆–0.5 H₂O: C, 53.63; H, 5.63; N, 11.73. Found: C, 53.67; H, 5.60; N, 11.65. The chiral salt (3.8 g, 10.9 mmol) was converted to the free acid by partitioning between 1N HCl, NaCl and EtOAC. The organic phase was separated, dried over MgSO₄, and concentrated in vacuo to give 2.15 g (10.1 mmol, 93%) of the title compound in >99.5% ee. α_D=–134° (c=0.01, MeOH). mp=260°–262° C. FDMS: M⁺+1=213. Anal. calcd. for C₈H₈N₂O₅: C, 45.29; H, 3.80; N, 13.20. Found: C, 45.48; H, 4.04; N, 13.13.

(f) 1S,4S,5R,6S-(+)-4-(spiro-5'-hydantoin)-2-oxabicyclo-[3.1.0]hexane-6-carboxylate. The mother liquors from step (e) were combined and concentrated in vacuo. The base addition salt was converted to the free acid by partitioning between 1N HCl, NaCl, and EtOAc. The organic phase was separated, dried over MgSO4, and concentrated in vacuo to give 2.2 g (10.4 mmol) of a solid. This solid was dissolved in hot EtOH (100 mL), and treated with a solution of S-(+)-2-phenylglycinol (1.56 g, 11.4 mmol) in EtOH (50 mL). After the initial precipitation of the salt, additional EtOH (50 mL) was added and refluxed. The chiral salt crystallized as the solution was allowed to cool to ambient temperature overnight to afford 2.4 g (6.9 mmol, 66%) in >99.5% ee. α_D=+103° (c=0.1, H2O). mp=217°–220° C. Anal. calcd. for C₁₆H₁₉N₃O₆–0.5 H2O: C, 53.63; H, 5.63; N, 11.73. Found: C, 53.87; H, 6.07; N, 10.69. The chiral salt (2.3 g, 6.6 mmol) was converted to the free acid by partitioning between 1N HCl, NaCl and EtOAC. The organic phase was separated, dried over MgSO4, and concentrated in vacuo to give 1.30 g (6.1 mmol, 93%) of the title compound in >99.5% ee. $\alpha_D$=+128° (c=0.01, MeOH). mp=267°-269° C. FDMS: M⁺+1=213. Anal. calcd. for $C_8H_8N_2O_5$·0.4 AcOH: C, 44.75; H, 4.10; N, 11.86. Found: C, 44.50; H, 4.06; N, 12.11.

(g) 1R,4R,5S,6R(−)-4-Amino-2-Oxabicyclo[3.1.0]hexane-4,6-dicarboxylic Acid. A solution of the product of step (e) (2.10 g, 10 mmol) in 2N NaOH (35 mL) was warmed at reflux overnight. The reaction mixture was then cooled to 0° C., acidified with 6N HCl to pH=1, and concentrated to dryness. The solid was reconstituted in $H_2O$ at pH=12 , applied to Bio-Rad® AG1-X8 anion exchange resin, and eluted with 3N AcOH to afford 1.51 g (8.07 mmol, 81%) of the title compound in >99.5% ee. mp>275° C. (dec.). $\alpha_D$=−63° (c=0.01, H2O). FDMS: M⁺+1=188. Anal. calcd. for $C_7H_9NO_5$: C, 44.93; H, 4.85; N, 7.48. Found: C, 44.66; H, 4.82; N, 7.36.

(h) 1S,4S,5R,6S(+)-4-Amino-2-Oxabicyclo[3.1.0]hexane-4,6-dicarboxylic Acid. A solution of the product of step (f) (1.20 g, 5.6 mmol) in 2N NaOH (15 mL) was warmed at reflux overnight. The reaction mixture was then cooled to 0° C., acidified with 6N HCl to pH=1, and concentrated to dryness. The solid was reconstituted in H2O at pH=12 , applied to Bio-Rad® AG1-X8 anion exchange resin, and eluted with 3N AcOH to afford 0.83 g (4.40 mmol, 79%) of the title compound in >99.5% ee. mp>275° C. (dec.). $\alpha_D$=+62° (c=0.01, H2O). FDMS: M⁺+1=188. Anal. calcd. for $C_7H_9NO_5$–0.3 H2O: C, 43.66; H, 5.03; N, 7.27. Found: C, 43.37; H, 4.68; N, 7.06.

EXAMPLE 3

1R,4R,5S,6R-4-Amino-2-Oxabicyclo[3.1.0]hexane-4,6-dicarboxylic Acid (a) 2S-1,2-O-Isopropylidene-butane-1,2,4-triol. A solution of S-(−)-1,2,4-butanetriol (25 g, 236 mmol) in acetone (500 mL) was treated in one portion with p-toluenesulfonic acid monohydrate (1.80 g, 9.4 mmol) and stirred at ambient temperature overnight. Triethylamine (0.95 g, 9.4 mmol) was added in one portion and the resulting reaction mixture concentrated in vacuo to yield the crude product. Purification via HPLC (10% EtOAc/hexanes to 90% EtOAC/hexanes) afforded the title compound (29.88 g, 204 mmol) 87%. $\alpha_D$=+2° (c=0.01, CH2Cl2). FDMS: M⁺+1=147. Anal. calcd. for $C_7H_{14}O_3$–0.25 H2O: C, 55.79; H, 9.70. Found: C, 55.80; H, 9.32.

(b) 5S, E-Ethyl 5,6-O-Isopropylidene-5,6-dihydroxy-2-hexanoate. Oxalyl chloride (38.71 g, 305 mmol) was added dropwise to a −78° C. solution of DMSO (31.75 g, 406 mmol) in $CH_2Cl_2$ (1 L) at a rate to maintain reaction temperature ≦−65° C. and subsequently stirred for an additional 30 minutes. To this reaction mixture was added dropwise a solution of the product of step (a) (29.7 g, 203 mmol) in $CH_2Cl_2$ (100 mL at a rate to maintain reaction temperature ≦−60° C.; upon complete addition the reaction mixture was stirred at −78° C. for 6 hours. Triethylamine (101 g, 1000 mmol) was added dropwise and the resulting slurry allowed to warm to ambient temperature as it stirred for 2 hours to afford crude O-Isopropylidene-4-oxo-(S)butane-1,2-diol. The reaction mixture was chilled to 0° C., (carbethoxymethylene)triphenyl-phosphorane (88.4 g, 250 mmol) was added in one portion, and allowed to warm to ambient temperature as it stirred overnight. The reaction mixture washed consecutively with $H_2O$, aqueous $NaHSO_4$, and brine, dried over $MgSO_4$ and concentrated in vacuo to yield the crude product. The product was triturated in $Et_2O$ (500 mL), the $Ph_3P$=O removed via filtration, and the filtrate concentrated in vacuo to yield the crude product. Purification via HPLC (10% EtOAc/hexanes) afforded the title compound (35.55 g, 166 mmol) 82%. $\alpha_D$=−9° (c=0.01, CH2Cl2). $\alpha_D$=−11° (c=0.01, MeOH). FDMS: M⁺=214. Anal. calcd. for $C_{11}H_{18}O_4$: C, 61.66; H, 8.47. Found: C, 61.53; H, 8.17.

(c) 5S, E-Ethyl-5,6-Dihydroxy-2-hexenoate. A solution of the product of step (b) (35.4 g, 165 mmol) in THF (330 mL) was treated in one portion with 1N HCl (330 mL) and stirred at ambient temperature overnight. The pH of the reaction was adjusted to 7 with $NaHCO_3$, then EtOAc and NaCl were added and the resulting slurry stirred vigorously for one hour. The reaction mixture was partitioned in a separatory funnel and the product extracted with EtOAc. All organics were combined, washed with brine, dried over $MgSO_4$, and concentrated in vacuo to yield the crude diol. Purification via HPLC (10% EtOAc/hexanes to 90% EtOAc/hexanes) afforded the title compound (24.6 g, 141 mmol) 86%. $\alpha_D$=−6° (c=0.01, CH2Cl2). $\alpha_D$=−22° (c=0.01, MeOH). FDMS: M⁺+1=175. Anal. calcd. for $C_8H_{14}O_4$·0.25 $H_2O$: C, 53.77; H, 8.18. Found: C, 53.50; H, 8.48

(d) 2R,4S-Ethyl 2-[(4-Hydroxytetrahydrofuran-2-yl)]-2-iodoacetate. A solution of the product of step (c) (24.6 g, 141 mmol) in diethyl ether (1 L) at ambient temperature was treated consecutively with $NaHCO_3$ (35.6 g, 424 mmol) then $I_2$ (80.7 g, 635 mmol), and the resulting reaction mixture stirred until complete by TLC. Solid $Na_2S_2O_3$ was added to the reaction mixture and stirred vigorously until discoloration occurred. The reaction mixture was partitioned with water and the product extracted with $Et_2O$. All organics were combined, washed with $Na_2S_2O_3$, $H_2O$, then brine, dried over $Na_2SO_4$ and concentrated in vacuo to yield the crude product. Purification via HPLC (10% EtOAc/hexanes to 50% EtOAc/hexanes) afforded the title compound (23.51 g, 78.3 mmol) 55%. $\alpha_D$=+64° (c=0.01, CHCl3). FDMS: M⁺=300. Anal. calcd. for $C_8H_{13}IO_4$·0.5 $H_2O$: C, 31.09; H, 4.57. Found: C, 30.89; H, 4.48.

(e) 2R-Ethyl 2-[(4-oxo-tetrahydrofuran-2-yl)]-iodoacetate. A 0° C. solution of the product of step (d) (23.3 g, 77.6 mmol) in acetone (500 mL) was treated by dropwise addition of Jones Reagent (225 mL, 450 mmol) at a rate to maintain the reaction temperature ≦10° C. Upon complete addition the reaction was allowed to warm to ambient temperature as it stirred for 6 hours. 2-Propanol (25 mL) was added dropwise to quench the reaction. The reaction volume was reduced in vacuo and the product extracted with Et2O. All organics were combined, washed with 10% NaHCO3, H2O, and brine, dried (MgSO4), and purified by prep HPLC (10% EtOAc/hexanes to 50% EtOAc/-hexanes) to afford 18.6 g, (62.3 mmol, 80%) of the title compound. $\alpha_D$=+65° (c=0.01, CHCl3). FDMS: M⁺=298. Anal. calcd. for $C_8H_{11}IO_4$: C, 32.24; H, 3.72. Found: C, 32.48; H, 3.62.

(f) 1R,5R,6R-Ethyl-2-oxabicyclo[3.1.0]hexan-4-one-6-carboxylate. A 10 ° C. solution of the product of step (e) (18.45 g, 61.9 mmol) in EtOAc (750 mL) was treated by dropwise addition of a solution DBU (11.78 g, 77.4 mmol) in EtOAc (75 mL) and the resulting reaction mixture stirred at 11° C. for 1 hour. The reaction mixture was acidified with 1N HCl, and the product extracted with EtOAc. All organics were combined, washed with Na2S2O3 then brine, dried over MgSO4, and concentrated in vacuo to yield the crude product. Purification via HPLC (10% EtOAc/hexanes to 50% EtOAc/-hexanes) afforded the title compound (6.62 g, 38.9 mmol) 63%. mp=88°-89° C. $\alpha_D$=+164° (c=0.01, CHCl3). FDMS: M⁺+1=171. Anal. calcd. for $C_8H_{10}O_4$: C, 56.47; H, 5.92. Found: C, 56.18; H, 5.65.

(g) 1R,4R,5S,6R-Ethyl-(4-spiro-5'-hydantoin)-2-oxabicyclo-[3.1.0]hexane-6-carboxylate. A room temperature solution of the product from step (f) (3.0 g, 17.6 mmol) in EtOH (25 mL) and H2O (10 mL), was treated consecutively with (NH4) 2CO3 (3.44 g, 44.1 mmol), and KCN (1.43 g, 22 mmol) and warmed at 35 ° C. for 1 hour. The pH of the reaction mixture was lowered to 1 with 5N HCl and concentrated to dryness. The product was recrystallized from 2-propanol/H2O (10:1), filtered, and dried under vacuum at 80° C. to afford 1.15 g (4.8 mmol, 27%) of the title compound. mp=195°–197° C. $\alpha_D$=–128° (c=0.01, MeOH). FDMS: M$^+$+1=241. Anal. calcd. for $C_{10}H_{12}N_2O_5$: C, 50.00; H, 5.04; N, 11.66. Found: C, 49.99; H, 4.89; N, 11.44.

(h) 1R,4R,5S,6R (4-spiro-5'-hydantoin)-2-oxabicyclo-[3.1.0]hexane-6-carboxylate. A solution of the product of Example g (1.10 g, 4.58 mmol) in 1N NaOH (15 mL) was stirred at ambient temperature for 3 hours. The reaction mixture was acidified to pH=1 with 5N HCl and the product extracted with EtOAc. All organics were combined, washed with brine, dried (MgSO4) and concentrated to afford 0.94 g (4.4 mmol, 97 of the title compound. $\alpha_D$=–139° (c=0.01, MeOH). mp=268°–270° C. FDMS: M$^+$+1=213. Anal. calcd. for $C_8H_8N_2O_5$–0.1 H2O: C, 44.91; H, 3.86; N, 13.09. Found: C, 44.80; H, 3.85; N, 12.92.

(i) 1R,4R,5S,6R-(–) 4-Amino-2-Oxabicyclo[3.1.0]hexane-4,6-dicarboxylic Acid. Utilizing 0.90 g (4.2 mmol) of product from step h, the title compound identical to the compound from example 2g, was obtained.

EXAMPLE 4

1SR,4RS,5RS,6RS-4-Amino-2-Thiabicyclo[3.1.0]hexane-4,6-dicarboxylic Acid (a) (1SR,5RS,6RS)-Ethyl [2-thiabicyclo[3.1.0]hex-3-ene]-carboxylate. A solution of ethyldiazoacetate (11.4 g, 100 mmol) in thiophene (20 mL) was added dropwise to a 70° C. solution of [Rh(OAc)$_2$]$_2$ in thiophene (100 mL). Upon complete addition, the reaction mixture was warmed under reflux for 3 hours, concentrated to an orange oil and purified by prep HPLC (10% EtOAc/hexanes) to afford 6.51 g (38%, 38.2 mmol) of the title compound. FDMS: M$^+$=170. Anal. calcd. for $C_8H_{10}O_2S$: C, 56.45; H, 5.92; S,18.84. Found: C, 56.72; H, 6.21; S,19.11.

(b) (1SR,4RS,5RS,6RS)-Ethyl 4-hydroxy-[2-thiabicyclo[3.1.0]-hexane]carboxylate. A solution of BH$_3$.THF (1M, 5.3 mmol) was added dropwise to a 0° C. solution of the product of step (a) (0.90 g, 5.29 mmol) in THF (25 mL), and subsequently stirred at 0° C. for 6 hours. 3N NaOH (5 mL) was added dropwise followed by 30% H$_2$O$_2$ (1 mL). The resulting reaction mixture was allowed to warm to ambient temperature as it stirred overnight. The reaction was partitioned with saturated NaHCO$_3$ and the product extracted with Et$_2$O. All organics were combined, washed with brine, dried (MgSO$_4$), and purified by PC-TLC (10% EtOAc/hexanes to 50% EtOAc/hexanes) to afford 0.48 g (48%, 2.5 mmol) of the title compound. FDMS: M$^+$=188. Anal. calcd. for $C_8H_{12}O_3S$.0.4 H2O: C, 49.16; H, 6.60; S,16.40. Found: C, 49.03; H, 6.28; S,17.80.

(c) (1SR,5RS,6RS)-Ethyl 4-oxo-[2-thiabicyclo[3.1.0]hexane]carboxylate. Oxalyl chloride (4.35 g, 34.3 mmol) was added dropwise to a –78° C. solution of DMSO (3.56 g, 45.6 mmol) in CH$_2$Cl$_2$ (400 mL) at a rate to maintain reaction temperature $\leq$–65° C. Upon complete addition the reaction was allowed to equilibrate for 30 minutes, followed by dropwise addition of a solution of the product of step (b) (4.31 g, 22.8 mmol) in CH$_2$Cl$_2$ (20 mL) maintaining reaction temperature $\leq$–65° C. The reaction was allowed to slowly warm to –40° C., after which time the reaction was once again chilled to –78° C., and quenched by dropwise addition of triethylamine (11.54 g, 114 mmol). The reaction was partitioned with 1N HCl and NaCl and the product extracted with Et$_2$O. All organic phases were combined, washed with H$_2$O, and brine, dried (MgSO$_4$) and purified by prep HPLC (10% EtOAc/hexanes to 50% EtOAc/hexanes) to afford 3.20 g (17.2 mmol, 75%) of the title compound. mp=55°–57° C. FDMS: M$^+$=186. Anal. calcd. for $C_8H_{10}O_3S$: C, 51.60; H, 5.41; S,17.23. Found: C, 51.59; H, 5.32; S,17.63.

(d) (1SR,4RS,5RS,6RS)-Ethyl 4-(spiro-5'-hydantoin)-[2-thiabicyclo[3.1.0]hexane]carboxylate. A solution of the product from step (c) (3.22 g, 17.3 mmol) in EtOH (25 mL) and H$_2$O (10 mL) at ambient temperature, was treated consecutively with (NH$_4$)$_2$CO$_3$ (3.37 g, 43.3 mmol), and KCN (1.41 g, 21.6 mmol) and warmed at 35° C. until reaction judged complete by TLC. The reaction mixture was acidified with 6N HCl, partitioned with NaCl and the product extracted with EtOAc. All organics were combined, dried (MgSO$_4$), and recrystallized from 2-propanol to afford 2.25 g (8.8 mmol, 51%) of the title compound. mp=197°–200° C. FDMS: M$^+$=256. Anal. calcd. for $C_{10}H_{12}N_2O_4S$.0.75 IPA: C, 48.83; H, 6.02; N, 9.30. Found: C, 48.75; H, 6.07; N, 8.94.

(e) (1SR,4RS,5RS,6RS) 4-Amino[2-thiabicyco[3.1.0]hexane]-4,6-dicarboxylate. A solution of the product from step (d) (0.85 g, 3.30 mmol) in 2N NaOH (20 mL) was warmed under reflux for 4 days. The reaction mixture was then acidified with 6N HCl and concentrated to dryness. The solid was reconstituted in H2O at pH=11, applied to Bio-Rad® AG1-X8 anion exchange resin, eluted with 3N AcOH, and concentrated to dryness. The product was triturated in hot H20/2-propanol mixture and filtered to afford 0.31 g, (46%, 1.5 mmol) of the title compound. mp>250° C. FDMS: M$^+$=203. Anal. calcd. for $C_7H_9NO_4S$.0.5 H2O: C, 39.62; H, 4.75; N, 6.60; S,15.11. Found: C, 39.81; H, 4.48; N, 6.69; S,14.27.

EXAMPLE 5

1R,4R,5S,6R-4-Amino-2-Oxabicyclo[3.1.0]hexane-4,6-dicarboxylic Acid (a) (1SR,5SR,6SR)-Ethyl-[2-oxabicyclo[3.1.0]hex-3-ene carboxylate. A solution of ethyldiazoacetate (100 g) in furan (250 mL) was added dropwise to a solution of [Rh(OAc)$_2$]$_2$ in furan (250 mL) with stirring at 10° C. over a period of about 2 to 2.5 hours. A further 0.1 g of [Rh(OAc)$_2$]$_2$ was added about two thirds of the way into the addition. After HPLC analysis showed complete consumption of ethyldiazoacetate, a solution of NaHSO$_3$ (200 g) in water (400 mL) was added, and the resultant two phase mixture was allowed to warm to ambient temperature with stirring for 1 to 2 hours. The reaction mixture was then extracted with MTBG (500 mL), and the organic phase washed with water (400 mL) and saturated NaCl (300 mL), then dried over Na$_2$SO$_4$. The solvent was then removed by evaporation, and the resultant oil was vacuum distilled (45° C. at 0.2 mm Hg) to afford the title compound (47–54 g) as an oil.

(b) (1SR,4RS,5SR,6SR)-Ethyl-4-hydroxy-[2-oxabicyclo-[3.1.0]hexane]carboxylate. A solution of thexylborane was prepared by adding a solution of 2,3-dimethyl-2-butene (4M, 53.0 mL) in THF via a syringe to borane dimethyl sulfide complex (10M, 21.2 mL) in a dry flask under nitrogen at below 0° C. The solution was stirred for 2 hours at <0° C. before use.

The product of step (a) (32.73 g, 212.30 mmol) was dissolved in 150 mL of THF under $N_2$. The resultant solution was cooled with stirring to –0.5° C. While the stirring solution was cooling, the system was evacuated and purged with $N_2$ twice. The entire thexylborane solution prepared above was added via cannula over 40 minutes, maintaining the temperature <4.4° C. After stirring 2 hours at 0° C., 87 mL of 30% $H_2O_2$ was added slowly, over 70 minutes, to maintain the temperature at <30° C. Following the peroxide addition, 15 mL of pH=7 phosphate buffer (1M $KH_2PO_4$ and 1M in $K_2HPO_4$) was added and the mixture was allowed to stir overnight (14 hours) while warming to ambient temperature. The mixture was cooled <5° C. and 25 mL of saturated aqueous $Na_2S_{23}$ was added slowly. 75 mL of EtOAc was then added, followed slowly by 75 mL of saturated aqueous $Na_2S_2O_3$. Another 40 mL of saturated aqueous $Na_2S_2O_3$ was then added slowly. The mixture was stirred for 15 minutes, then partitioned between 75 mL of EtOAc and 30 mL of saturated aqueous $Na_2S_2O_3$. The aqueous layer was back extracted three times with 50 mL of EtOAc. The combined organic layers were washed with 30 mL of brine and dried over $Na_2SO_4$. The solvent was removed to afford 54.44 g of an oil. The oil was purified by a flash chromatography (370 g of silica gel, wet packed with 3:2 hexanes: EtOAc) eluting with 3:2 hexanes: EtOAc, to afford 31.72 g of the title compound as an oil.

(c) (1SR,5SR,6SR)-Ethyl 4-oxo-[2-oxabicyclo[3.1.0]-hexane]carboxylate. Oxalyl chloride (25.70 g, 202.44 mmol) in $CH_2Cl_2$ (300 mL) under $N_2$ was added dropwise over 35 minutes to a solution of DMSO (28.74 g, 367.8 mmol) while keeping the temperature below <–65° C. The solution was stirred for 10 minutes, and cooled back to –70° C. A solution of 31.68 g of the product of step (b) (26.29 g, 152.71 mmol corrected for 83% potency) dissolved in 100 mL of $CH_2Cl_2$ was added dropwise over 40 minutes while maintaining the temperature at –67° C. The mixture was stirred for 5 minutes, then 62 mL (45.01 g, 444.83 mmol) of triethylamine was added dropwise over 15 minutes, keeping the temperature below –50° C. After stirring for 15 minutes, TLC indicated complete reaction and the mixture allowed to warm to about –40° C. The mixture was filtered, and washed through with 300 mL of $CH_2Cl_2$. The filtrate was extracted two times with 150 mL of 1N HCl. The aqueous layer was back extracted with 50 mL of $CH_2Cl_2$. The combined organic layers were washed with 75 mL of brine and dried over $Na_2SO_4$. Most of the solvent was removed by rotary evaporation to leave 44.36 g of liquid. A few seed crystals were added and the flask was blanketed with $N_2$ and stirred ambient temperature for 30 minutes while a thin slurry formed. To the room temperature slurry was slowly added 20 mL of hexanes. The slurry was stirred 90 minutes at ambient temperature then 3 hours in an ice/NaCl/water bath. The solids were filtered, washed with 25 mL of 5:1 hexanes: EtOAc, and dried under vacuum to afford the title compound (19.48 g) as white crystals. A second crop of crystals (2.28 g) was obtained from the filtrate.

(d) (1SR,4SR,5RS,6SR)-Ethyl 4-(spiro-5'-hydantoin)-2-oxabicyclo[3.1.0]hexane carboxylate. To a slurry of ammonium carbonate (5.65 g, 58.8 mmol), potassium cyanide (2.01 g, 30.9 mmol) in 25 mL of methanol at ambient temperature was added a solution of the product of step (c) (5.0 g, 29.4 mmol) in 25 mL of methanol. The mixture was stirred at ambient temperature and monitored by HPLC. After 23 hours the reaction was complete. The mixture was diluted with 100 mL of water, cooled and seeded. The pH was adjusted from 9.6 to 7.0 with 6N hydrochloric acid giving a white solid. The slurry was stirred at 0°–5° C. for 1.5 hours, filtered and washed with 75 mL of cold water-methanol (2:1). The white solid was dried in vacuo at 40° C. affording the title compound (5.55 g, 78.6%). The product was identified by $^1H$ NMR.

(e) (1SR,4SR,5RS,6SR)-4-(spiro-5'-hydantoin)-2-oxabicyclo[3.1.0]hexane carboxylic acid. A solution of the product of step (d) (7.59 g, 31.6 mmol) in 2N NaOH (63.2 mL) was stirred for 30 minutes at ambient temperature. The hydrolysis was then quenched by the addition 12N HCl (5.27 mL, 63.2 mmol). The reaction mixture was then stirred for three hours at 0° C., then vacuum filtered. The solid collected was dried under vacuum at 50° C. overnight, affording the title compound (6.12 g, 91.3%). 1H NMR (DMSO-$d_6$) δ2.24 (s, 1H), 2.26 (s, 1H), 3.35 (d, 1H, J=11 Hz), 4.05 (d, 1H, J =11 Hz), 4.39 (d, 1H, J=5 Hz). $^{13}C$ NMR (DMSO-$d_6$) δ22.14, 30.75, 65.74, 68.32, 70.61, 156.32, 171.11, 175.63. Anal Calcd for $C_8H_8N_2O_5$: C, 45.29; H, 3.80; N, 13.2. Found: C, 45.02; H, 3.75; N, 12.92.

(f) 1R,4R,5S,6R-(–)-4-spiro-5'-hydantoin-2-oxabicyclo[3.1.0]hexane carboxylic acid, (R)-(–)-2-phenylglycinol salt. To the product of step (e), (0.80 g, 3.8 mmol) was added (R)-(–)-phenylglycinol (0.52 g, 3.8 mmol) in ethanol (20 mL) and water (4 mL). The mixture was heated to reflux, and an additional 1 mL of water was added, producing a homogenous solution. After approximately 30 minutes at reflux, the mixture was allowed to cool to ambient temperature. After stirring at ambient temperature overnight, the reaction mixture was filtered, washed with 1 mL of a cold 25:5 mixture of ethanol and water, and dried under vacuum at 50° C. overnight, to afford the title compound (0.57 g, 43.3%) as a white solid. $^1H$ NMR (DMSO-$d^6$) δ2.05 (t, 1H, J=3.3 Hz), 2.20 (d, 1H, J=3 Hz), 3.30 (d, 1H, J=11 Hz), 3.50 (m, 1H), 3.55 (m, 1H), 4.0 (d, 1H, J=11 Hz), 4.1 (m, 1H), 4.18 (d, 1H, J=6 Hz), 7.25 (m, 1H), 7.30 (m, 2H), 7.35 (m, 2H). Enantiomeric excess was determined to be 98.8% by HPLC.

(g) 1R,4R,5S,6R-(–)-4-Amino-2-oxabicyclo[3.1.0]hexane-4,6-dicarboxylic acid. To the product of step (f) (1.0 g, 2.86 mmol) was added 15 mL (30 mmol, 10 eq) of 2M aqueous sodium hydroxide. The solution was heated at reflux for 43 hours. The resulting mixture was allowed to cool to ambient temperature, then extracted with $CH_2Cl_2$ (5×30 mL). The aqueous layer was diluted with 10 mL of $H_2O$ and acidified to pH2 with 3M HCl. The cloudy mixture was filtered, and the pH was adjusted to 8 using 2M NaOH, then the solution was allowed to stand over the weekend. This resulted in formation of a gel from the remaining silicic acid. The gel was removed by filtration through a medium glass frit over 1 hour and rinsed with 50 mL of $H_2O$.

An ion exchange column was prepared from 25 g of Bio-Rad AG 1-X8, 100–200 mesh, acetate form, resin. The resin was transferred to a gravity flow column using deionized $H_2O$ and washed sequentially with 1M NaOH (2×50 mL) and $H_2O$ (2×50 mL or until eluent neutral). The aqueous product solution was poured onto the resin in 50 mL portions. The column was washed sequentially with $H_2O$ until the eluent was neutral (about 100 mL), 70 mL of 1:1 THF/$H_2O$, and 100 mL of $H_2O$. The product was eluted with 120 mL of a 1:3 mixture of acetic acid and $H_2O$. The entire eluent was collected in one flask and evaporated to 0.48 g of a white solid. The solid was slurried in 5 mL of $H_2O$ and collected on a coarse glass frit. The flask was rinsed with additional $H_2O$ (2×5 mL) and these rinsings were used to wash the collected solid. After drying under vacuum at 70° C. for 18 hours, the title compound (0.33 g, 62%) was obtained as a white solid. The structure was confirmed by $^1H$ NMR and analysis.

EXAMPLE 6

1SR,4RS,5RS,6RS-4-Amino- (2-sulfonylbicyclo [3.1.0]hexane)-4,6-dicarboxylic Acid (a) (1SR,4RS,5RS,6RS) Ethyl (4-spiro-5'-hydantoin)-[2-sulfonylbicyclo[3.1.0]hexane]-6-carboxylate. m-CPBA (1.56 g, 5.0 mmol) was added in one portion to a room temperature solution of the product from Example 4(d) (0.51 g, 2.0 mmol) in EtOAc (50 mL) and stirred at room temperature until the reaction was judged complete by TLC. The reaction was diluted with 10% NaHCO3 and the product extracted with EtOAC. All organics were combined, washed with brine, dried over Na2SO4, and purified by prep HPLC (10% EtOAC/hexanes to 50% EtOAc/hexanes) to afford 0.21 g (0.73 mmol, 36%) of the title compound. mp>275° C. FDMS: M$^+$=288. Anal. calcd. for $C_{10}H_{12}N_2O_6S$.0.4 m-chlorobenzoic acid: C, 43.81; H, 4.02; N, 7.98; S.9.14. Found: C, 43.87; H, 4.04; N, 7.96; S, 9.44.

(b) (1SR,4RS,5RS,6RS) 4-Amino-(2-sulfonylbicyclo [3.1.0]-hexane)-6-carboxylate. A solution of the product of (a) (0.14 g, 0.49 mmol) in 2N NaOH (10 mL) was warmed under reflux overnight. The reaction mixture was acidified to pH=1 with 5N HCl and concentrated to dryness. The product was reconstituted in H2O at pH=12, applied to BioRad® AG1-X8 anion exchange resin, and eluted with 3N AcOH to afford 0.10 g (87%, 0.43 mmol) of the title compound. mp=>250° C. FDMS: M$^+$+1=236. Anal. calcd. for $C_7H_9NO_6S$.0.5 H2O: C, 34.43; H, 4.13; N, 5.74. Found: C, 34.29; H, 3.98; N, 5.45.

EXAMPLE 7

1SR,3RS,4SR,5RS,6SR-3-((3-chloro-4-fluoro) benzyl)-4-amino-2-oxabicyclo[3.1.0]hexane-4,6-dicarboxylic Acid (a) 1SR,5SR,6SR-Ethyl-3-((3-chloro-4-fluoro) benzylidenyl)-2-oxabicyclo[3.1.0]hexan-4-one-6-carboxylate. A solution of the product of Example 1(f) (4.3 g, 25.2 mmole), 3-chloro-4-fluorobenzaldehyde (8.0 g, 50.4 mmol and pyrrolidine (0.9 g, 12.6 mmol) in EtOH (100 mls) was stirred at room temperature for 18 h. The reaction mixture was concentrated to dryness and the residue was purified by HPLC (5% EtOAc/hexane to 50% EtOAc/ hexane) yielding 4.2 g (53%) of the title compound. mp=110°-112° C. FDMS: M$^+$=310. Anal. calcd. for $C_{15}H_{12}ClFO_4$: C, 57.99; H, 3.89. Found: C, 57.92; H, 3.75.

(b) 1SR,3SR,5SR,6SR-Ethyl-3-((3-chloro-4-fluoro) benzyl)-2-oxabicyclo[3.1.0]hexan-4-one-6-carboxylate and 1SR,3RS,5SR,6SR-Ethyl-3-((3-chloro-4-fluoro)benzyl)-2-oxabicyclo[3.1.0]hexan-4-one-6-carboxylate. The title mixture of compounds was prepared employing the product of step (a) (8.8 g, 28.3 mmol), Raney Ni (0.2 g), EtOAc and hydrogen at 40 psi for 15 minutes. Due to over reduction of the ketone the crude product was oxidized using pyridinium chlorochromate and powdered sieves yielding 6.8 g of crude ketone. The residue was purified by HPLC (5% EtOAc/ hexane to 50% EtOAc/hexane) yielding 5.2 g (58%) of the title mixture of compounds. FDMS: M$^+$=312. Anal. calcd. for $C_{15}H_{14}ClFO_4$.: C, 57.61; H, 4.51. Found: C, 56.98; H, 4.70.

(c) 1SR,3RS,4SR,5RS,6SR - Ethyl-3-((3-chloro-4-fluoro) -benzyl)-(4-spiro-5'-hydantoin)-2-oxabicyclo[3.1.0]hexane-6-carboxylate. The title compound was prepared employing the product of step (b) (1.0 g, 3.2 mmol), ammonium carbonate (0.75 g, 9.6 mmol) and KCN (0.25 g, 3.8 mmol) in a 1:1 EtOH/water mixture. The reaction mixture was heated at 35°-40° C. for 48 h. The reaction mixture was partitioned between water and EtOAc. After extraction with EtOAc, the organic layer was dried with MgSO4, concentrated and purified using radial chromatography (EtOAc/ Hexane) to yield 0.18 g (14%) of the product hydantoin. Crystallization of the product from chloroform yielded white solids. mp=224°-226° C. FDMS: M$^+$=382. Anal. calcd. for $C_{17}H_{16}ClFN_2O_5$.−0.5 CHCl3: C, 47.51; H, 3.75; N, 6.33. Found: C, 47.87; H, 3.69; N, 6.22.

(d) 1SR,3RS,4SR,5RS,6SR-3-((3-chloro-4-fluoro) benzyl)-4-amino-2-oxabicyclo[3.1.0]hexane-4,6-dicarboxylic acid. The title compound was prepared employing the product of step (c) (0.1 g, 0.26 mmol) and 1N NaOH (10 ml) at reflux for 48 h. The reaction mixture was adjusted to a pH=10 with 1N HCl and anion exchange performed on the crude product. The product was recrystallized from H2O and dried in a vacuum oven at 70° C. to yield 8 mg (9%) of the title compound. mp=250°-251° C. FDMS: M$^+$=330.

We claim:

1. A compound of the formula

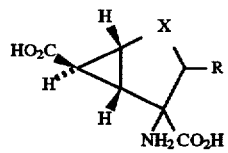

in which X represents O, NR$^a$, S, SO or SO$_2$; R represents a hydrogen atom; a (1–6C) alkyl group; a (2–6C) alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C) alkenyl or (2–6C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; R$^a$ represents hydrogen or a group of formula (CO)$_n$R$^b$; n is 0 or 1; and R$^b$ is as defined for R; or a non-toxic metabolically labile ester or amide thereof; or a pharmaceutically acceptable salt thereof.

2. A compound as claimed in claim 1, in which R$^a$ represents hydrogen.

3. A compound as claimed in claim 1, in which X represents O or S.

4. A compound as claimed in claim 1, in which R represents a hydrogen atom or a phenyl (1–4C) alkyl or diphenyl(1–4C) alkyl group which is unsubstituted or substituted on phenyl by one or two substituents selected independently from halogen, (1–4C) alkyl, (1–4C) alkoxy and phenyl.

5. A compound as claimed in claim 1, which has the stereochemistry shown below.

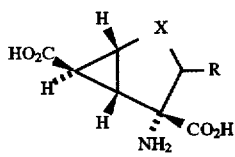

6. A compound as claimed in claim 1, in which R represents a hydrogen atom.

7. A compound as claimed in claim 1, which is selected from 1SR,4SR,5RS,6SR-4-amino-2-oxabicyclo[3.1.0]hexane-4,6-dicarboxylic acid; 1SR,4SR,5RS,6SR-4-amino-2-thiabicyclo-[3.1.0]hexane-4,6-dicarboxylic acid, 1SR, 4RS,5RS-4-amino-(2-sulfonylbicyclo[3.1.0]hexane)-4,6-dicarboxylic acid and 1SR,3RS,4SR,5RS,6SR-3-((3-chloro-4-fluorobenzyl)-4-amino-2-oxabicyclo[3.1.0]hexane-4,6-dicarboxylic acid.

8. The compound claimed in claim 1, which is 1R,4R, 5S,6R-4-Amino-2-oxabicyclo[3.1.0]hexane-4,6-dicarboxylic acid.

9. A process for the preparation of a compound of formula I which comprises (a) hydrolyzing a compound of formula

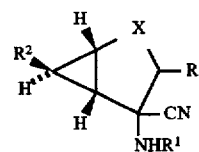

II in which $R^1$ represents a hydrogen atom or an acyl group and $R^2$ represents a carboxyl group or an esterified carboxyl group, or a salt thereof;

(b) hydrolyzing a compound of formula

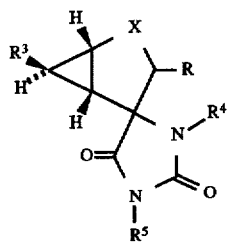

III in which $R^3$ represents a carboxyl group or an esterified carboxyl group, and $R^4$ and $R^5$ each independently represent a hydrogen atom, a (2–6C) alkanoyl group, a (1–4C) alkyl group, a (3–4C) alkanoyl group or a phenyl (1–4C) alkyl group in which the phenyl is unsubstituted or substituted by halogen, (1–4C) alkyl or (1–4C) alkoxy, or a salt thereof; or (c) deprotecting a compound of formula

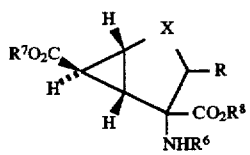

IV in which $R^6$ represents a hydrogen atom or a nitrogen protecting group and each of $R^7$ and $R^8$ independently represent a hydrogen atom or a carboxyl protecting group, or a salt thereof;

whereafter, if necessary and/or desired (i) resolving the compound of formula I;

(ii) converting the compound of formula I into a non-toxic metabolically labile ester or amide thereof; and/or;

(iii) converting the compound of formula I or a non-toxic metabolically labile ester or amide thereof into a pharmaceutically acceptable salt thereof.

10. A pharmaceutical formulation, which comprises a compound as claimed in claim 1 and a pharmaceutically acceptable carrier, diluent or excipient.

11. A method of modulating one or more metabotropic glutamate receptor functions in a warm blooded mammal requiring such treatment, which comprises administering an effective amount of a compound as claimed in claim 1.

12. A compound of the formula

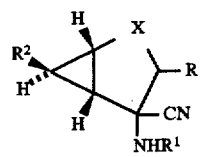

II in which X represents O, $NR^a$, S, SO or $SO_2$; R represents a hydrogen atom; a (1–6C) alkyl group; a (2–6C) alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C) alkenyl or (2–6C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_nR^b$; n is 0 or 1; and $R^b$ is as defined for R; $R^1$ represents a hydrogen atom or an acyl group and $R^2$ represents a carboxyl group or an esterified carboxyl group, or a salt thereof.

13. A compound of the formula

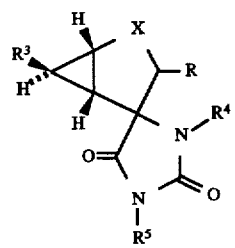

III in which X represents O, $NR^a$, S, SO or $SO_2$; R represents a hydrogen atom; a (1–6C) alkyl group; a (2–6C) alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C) alkenyl or (2–6C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_nR^b$; n is 0 or 1; and $R^b$ is as defined for R; $R^3$ represents a carboxyl group or an esterified carboxyl group, and $R^4$ and $R^5$ each independently represent a hydrogen atom, a (2–6C) alkanoyl group, a (1–4C) alkyl group, a (3–4C) alkenyl group or a phenyl (1–4C) alkyl group in which the phenyl is unsubstituted or substituted by halogen, (1–4C) alkyl or (1–4C) alkoxy, or a salt thereof.

14. A compound of the formula

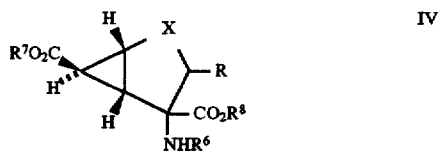

IV in which X represents O, $NR^a$, S, SO or $SO_2$; R represents a hydrogen atom; a (1–6C) alkyl group; a (2–6C) alkenyl group; a (2–6C) alkynyl group; an optionally substituted aromatic group; an optionally substituted heteroaromatic group; a non-aromatic carbocyclic group; a non-aromatic heterocyclic group; a non-aromatic monocyclic carbocyclic group fused with one or two monocyclic aromatic or heteroaromatic groups; a non-aromatic monocyclic heterocyclic group fused with one or two monocyclic aromatic or heteroaromatic groups; or a (1–6C) alkyl, (2–6C) alkenyl or (2–6C) alkynyl group which is substituted by one, two or three groups selected independently from an optionally substituted aromatic group, an optionally substituted heteroaromatic group, a non-aromatic carbocyclic group, a non-aromatic heterocyclic group, a non-aromatic monocyclic carbocyclic group fused with one or two monocyclic aromatic or heteroaromatic groups and a non-aromatic monocyclic heterocyclic group fused with one or two monocyclic aromatic or heteroaromatic groups; $R^a$ represents hydrogen or a group of formula $(CO)_nR^b$; n is 0 or 1; and $R^b$ is as defined for R; $R^6$ represents a hydrogen atom or a nitrogen protecting group and each of $R^7$ and $R^8$ independently represent a hydrogen atom or a carboxyl protecting group, or a salt thereof.

* * * * *

UNITED STATES PATENT AND TRADEMARK OFFICE
CERTIFICATE OF CORRECTION

PATENT NO. : 5,688,826
DATED : Nov. 18, 1997
INVENTOR(S) : Steven Marc Massey, et al.

It is certified that error appears in the above-identified patent and that said Letters Patent is hereby corrected as shown below:

Column 14, line 13, delete "74.6 mmol" and insert therefor-- 174.6 mmoL--.

Column 15, line 43, delete "$\leq$" and insert therefore-- $\leq$ --.

Column 19, line 22, insert % after 97.

Column 21, line 16, delete "$Na_2S_23$" and insert therefore-- $Na_2S_2O_3$ --.

Signed and Sealed this

First Day of December, 1998

Attest:

BRUCE LEHMAN

Attesting Officer

Commissioner of Patents and Trademarks